United States Patent
Katafuchi

(10) Patent No.: US 8,854,058 B2
(45) Date of Patent: Oct. 7, 2014

(54) MEASUREMENT METHOD OF DEGRADATION/ALTERATION DEGREE OF LUBRICANT OIL AND MEASUREMENT DEVICE THEREOF

(75) Inventor: Tadashi Katafuchi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 183 days.

(21) Appl. No.: 13/510,652

(22) PCT Filed: Nov. 22, 2010

(86) PCT No.: PCT/JP2010/070842
§ 371 (c)(1),
(2), (4) Date: May 18, 2012

(87) PCT Pub. No.: WO2011/065340
PCT Pub. Date: Jun. 3, 2011

(65) Prior Publication Data
US 2012/0229151 A1 Sep. 13, 2012

(30) Foreign Application Priority Data
Nov. 25, 2009 (JP) .................. 2009-268119

(51) Int. Cl.
- *G01N 27/416* (2006.01)
- *G01R 27/26* (2006.01)
- *G01R 27/08* (2006.01)
- *F01M 11/10* (2006.01)
- *G01N 27/22* (2006.01)
- *G01N 33/28* (2006.01)

(52) U.S. Cl.
CPC ........... *G01N 33/2888* (2013.01); *F01M 11/10* (2013.01); *G01N 27/221* (2013.01); *F16N 2250/30* (2013.01); *F01M 2011/1413* (2013.01)
USPC ............ 324/672; 324/438; 324/663; 324/698

(58) Field of Classification Search
CPC .......... F01M 11/10; F01M 2011/1413; G01N 33/2888; G01N 27/221; F16N 2250/30
USPC ................... 324/672, 698, 438, 663
See application file for complete search history.

(56) References Cited

U.S. PATENT DOCUMENTS 6,459,995 B1 * 10/2002 Collister .................... 702/23
6,549,015 B2 * 4/2003 Horie et al. .................. 324/438

(Continued)

FOREIGN PATENT DOCUMENTS

| EP | 1 014 082 A2 | 6/2000 |
|----|--------------|--------|
| JP | 10 078402    | 3/1998 |

(Continued)

OTHER PUBLICATIONS

JP2003-114206, Apr. 2003, Nakamura et al. (Machine translation attached).*

(Continued)

*Primary Examiner* — Melissa Koval
*Assistant Examiner* — Farhana Hoque
(74) *Attorney, Agent, or Firm* — Oblon, Spivak, McClelland, Maier & Neustadt, L.L.P.

(57) ABSTRACT

Provided is a method of measuring a degree of degradation/alteration of a lubricating oil, including obtaining dielectric constants or electrostatic capacitances at two or more different frequencies and determining a degradation/alteration state of the lubricating oil based on values of the dielectric constants or the electrostatic capacitances, in which one frequency ($H_1$) of the two or more frequencies is in a range of 1 to 100 Hz, and another frequency ($H_2$) is more than the frequency ($H_1$) and in a range of 10,000 Hz or less. Accordingly, it is possible to provide a method of measuring a degree of degradation/alteration of a lubricating oil and a measuring device therefor, which are capable of measuring a degree of degradation of the lubricating oil easily and precisely and predicting a degradation/alteration mechanism of the lubricating oil.

12 Claims, 2 Drawing Sheets

(56) References Cited

U.S. PATENT DOCUMENTS

| | | |
|---|---|---|
| 2004/0075448 A1 | 4/2004 | Lvovich et al. |
| 2004/0085080 A1 | 5/2004 | Schilowitz et al. |
| 2004/0239344 A1 | 12/2004 | Hu |
| 2004/0250606 A1 | 12/2004 | Buttgenbach et al. |
| 2009/0157345 A1 | 6/2009 | Yoshioka et al. |
| 2009/0315574 A1 | 12/2009 | Akiyama et al. |
| 2011/0074452 A1 | 3/2011 | Katafuchi |

FOREIGN PATENT DOCUMENTS

| | | |
|---|---|---|
| JP | 2001 526781 | 12/2001 |
| JP | 2003 114206 | 4/2003 |
| JP | 2004 537737 | 12/2004 |
| JP | 2005 507497 | 3/2005 |
| JP | 2005 529333 | 9/2005 |
| JP | 2009 2693 | 1/2009 |
| JP | 2009 145131 | 7/2009 |
| WO | WO 03/104798 A1 | 12/2003 |

OTHER PUBLICATIONS

International Search Report Issued Mar. 1, 2011 in PCT/JP10/70842 Filed Nov. 22, 2010.

Extended European Search Report issued May 2, 2014 in Patent Application No. 10833186.9.

Chistian Ulrich et al., "Simultaneous Estimation of Soot and Diesel Contamination in Engine Oil Using Electrochemical Impedance Spectroscopy", Sensors and Actuators B: Chemical: International Journal Devoted to Research and Development of Physical and Chemical Transducers, vol. 127, No. 2, XP-022308702, Oct. 22, 2007, pp. 613-618.

* cited by examiner

MEASUREMENT METHOD OF DEGRADATION/ALTERATION DEGREE OF LUBRICANT OIL AND MEASUREMENT DEVICE THEREOF

TECHNICAL FIELD

The present invention relates to a method of measuring a degree of degradation/alteration of a lubricating oil. More specifically, the present invention relates to a method of measuring a degree of degradation/alteration of a lubricating oil, which is capable of measuring a degree of degradation/alteration of a lubricating oil and predicting a degradation/alteration mechanism, and to a measuring device therefor.

BACKGROUND ART

The degree of degradation/alteration of a lubricating oil has large effects on the performance and durability of a machine and a device that use the lubricating oil, and on the performance of energy saving. Further, the progression speed of degradation/alteration of the lubricating oil varies considerably depending upon the condition under which the lubricating oil is used. Therefore, it is necessary that the degradation/alteration state of the lubricating oil can be measured easily and precisely.

Conventionally, in order to measure the degree of degradation/alteration of the lubricating oil such as an engine oil, there have been used a method in which an operating time of the lubricating oil is used as a measure and a method in which properties (e.g., a kinetic viscosity, an insoluble content, an acid number, a base number) of the lubricating oil are measured and a degree of degradation is determined based on the measurement result. However, those methods cannot measure a degree of degradation/alteration of the lubricating oil easily and precisely.

In order to solve the above-mentioned problem, for example, Patent Document 1 discloses a method in which a resistance sensor is installed in an oil pan and the lifetime of the lubricating oil is measured based on a change in electric resistance of an engine oil. Further, there are also disclosed a large number of methods in which a pH sensor is installed in an oil pan and the lifetime of the lubricating oil is measured based on a change in pH involved in a change in acidity and basicity of an oil.

Those methods are simple because a change in electric resistance and a change in pH in the lubricating oil can be checked on a steady basis, and it can be determined that the lifetime has expired at a time when a change rate of the electric resistance or pH has reached a predetermined value or state.

However, the electric resistance also fluctuates due to the contamination of soot (carbon), which is not a polar substance generated along with the degradation/alteration of the lubricating oil, and hence, the degree of degradation/alteration of the lubricating oil may not be measured precisely. Further, even if the pH indicates the degree of degradation/alteration, a clue for determining a cause of degradation/alteration (degradation/alteration mechanism) that has degraded the lubricating oil cannot be obtained from the pH. Thus, there is a problem in terms of the management of degradation/alteration of the lubricating oil.

In recent years, a research is being conducted for measuring a degree of degradation/alteration of the lubricating oil by measuring an impedance of the lubricating oil and also for clarifying the influence of the contamination of soot.

For example, in Non-Patent Document 1, an impedance of the lubricating oil in a wide frequency range of 20 Hz to 600 kHz is measured, and a change in impedance caused by the contamination of soot or diesel is studied with the impedance being divided into a resistance (resistance component) and a reactance (capacitance component). However, the study result has not clearly found out a relationship between the concentration of soot or diesel and the impedance.

Patent Document 2 discloses a device for measuring a complex impedance of an oil, obtaining an electric conductivity with the assumption that a real part of an inverse number of the complex impedance is a resistance component, obtaining a dielectric constant with the assumption that an imaginary part of the inverse number of the complex impedance is a capacitance component, and detecting degradation/alteration in an oil from the electric conductivity and the dielectric constant.

However, according to the method described in Patent Document 2, it is difficult to measure a degree of degradation/alteration from a measured value of a dielectric constant precisely and analyze a degradation/alteration mechanism (cause of degradation/alteration) of the lubricating oil.

Further, there is also a problem in that the device for measuring an impedance disclosed in Non-Patent Literature 1 and Patent Literature 2 has a complicated measurement circuit, which results in high cost of the device.

BACKGROUND ART

Patent Document

[Patent Document 1] JP 10-78402 A
[Patent Document 2] JP 2009-2693 A

Non-Patent Literature

[Non-Patent Document 1] Sensors and Actuators, B127 (2007), 613-818

SUMMARY OF THE INVENTION

Problem to be solved by the Invention

Under such circumstances, it is an object of the present invention to provide a method of measuring a degree of degradation/alteration of a lubricating oil, which is capable of measuring a degree of degradation/alteration of the lubricating oil easily and precisely and predicting a degradation/alteration mechanism of the lubricating oil, and also provide a measuring device therefor.

Means for Solving the Problem

The inventors of the present invention earnestly studied so as to achieve the above-mentioned object, and consequently, found that a dielectric constant and an electrostatic capacitance in a particular low frequency region of a lubricating oil changes depending upon an amount of a polar substance generated due to degradation/alteration of the lubricating oil and that a state of a change in dielectric constant or electrostatic capacitance with respect to a frequency of the lubricating oil gives information on a degradation/alteration mechanism (cause of degradation/alteration) of the lubricating oil. The present invention has been achieved based on such findings.

That is, the present invention provides:

[1] a method of measuring a degree of degradation/alteration of a lubricating oil, including obtaining dielectric constants or electrostatic capacitances at two or more different frequencies and determining a degradation/alteration state of the lubricating oil based on values of the dielectric constants or the electrostatic capacitances, in which one frequency ($H_1$) of the two or more different frequencies is in a range of 1 to 100 Hz, and another frequency ($H_2$) is more than the one frequency ($H_1$) and in a range of 10,000 Hz or less;

[2] the method of measuring a degree of degradation/alteration of a lubricating oil according to the above-mentioned item [1], in which the frequency ($H_1$) is in a range of 5 to 80 Hz, and the frequency ($H_2$) is more than the frequency ($H_1$) and in a range of 1,000 Hz or less;

[3] the method of measuring a degree of degradation/alteration of a lubricating oil according to the above-mentioned item [1] or [2], further including: obtaining a dielectric constant ($\epsilon_1$) or an electrostatic capacitance ($C_1$) at the frequency ($H_1$) and a dielectric constant ($\epsilon_2$) or an electrostatic capacitance ($C_2$) at the frequency ($H_2$); determining that the lubricating oil has been degraded/altered when a value of the dielectric constant ($\epsilon_1$) or the electrostatic capacitance ($C_1$) or a value of the dielectric constant ($\epsilon_2$) or the electrostatic capacitance ($C_2$) has reached a set value; and predicting a degradation/alteration mechanism of the lubricating oil based on a rate of a change in dielectric constant with respect to the frequency $[(\epsilon_1-\epsilon_2)/(H_2-H_1)]$ or a rate of a change in electrostatic capacitance with respect to the frequency $[(C_1-C_2)/(H_2-H_1)]$;

[4] a device for measuring a degree of degradation/alteration of a lubricating oil, including: a pair of electrodes; an AC power source for applying an AC voltage between the pair of electrodes under control of a frequency to a region of 100 Hz or less; and an electrostatic capacitance measuring part including an electrostatic capacitance measuring circuit for measuring an electrostatic capacitance between the pair of electrodes;

[5] the device for measuring a degree of degradation/alteration of a lubricating oil according to the above-mentioned item [4], further including a dielectric constant calculating part including a dielectric constant calculating circuit for calculating a dielectric constant based on the electrostatic capacitance obtained in the electrostatic capacitance measuring part;

[6] the device for measuring a degree of degradation/alteration of a lubricating oil according to the above-mentioned item [4] or [5], in which the pair of electrodes are comb-shaped electrodes; and

[7] a lubricating oil monitoring system for a machine and a device, including the device for measuring a degree of degradation/alteration of a lubricating oil according to any one of the above-mentioned items [4] to [6].

Effects of the Invention

According to the present invention, it is possible to provide a method of measuring a degree of degradation/alteration of a lubricating oil, which is capable of measuring a degree of degradation/alteration of the lubricating oil easily and precisely and predicting a degradation/alteration mechanism of the lubricating oil.

[FIG.] 3 A conceptual diagram illustrating one example of a device for measuring a degree of degradation/alteration of a lubricating oil of the present invention (electrostatic capacitance measuring part and dielectric constant calculating part).

Figure 4:
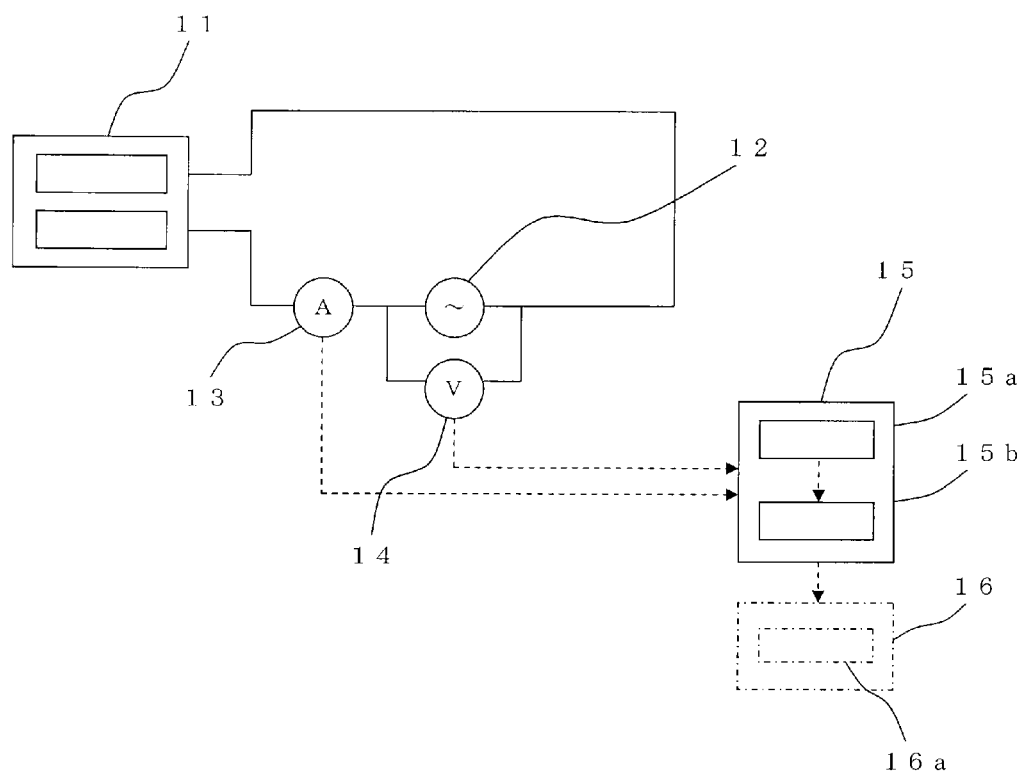

[FIG. 4] A conceptual diagram illustrating another example of the device for measuring a degree of degradation/alteration of a lubricating oil of the present invention (electrostatic capacitance measuring part and dielectric constant calculating part).

MODE FOR CARRYING OUT THE INVENTION

The present invention is a method of measuring a degree of degradation/alteration of a lubricating oil, including measuring dielectric constants or electrostatic capacitances of a lubricating oil at two or more different frequencies and determining a degradation/alteration state of the lubricating oil based on values of the dielectric constants or the electrostatic capacitances.

The phrase "determining a degradation/alteration state of a lubricating oil" in the present invention refers to measuring a degree of degradation/alteration of a lubricating oil and also predicting a degradation/alteration mechanism (cause of degradation/alteration). Through both the measurement and the prediction, the lifetime of a lubricating oil in use can be predicted precisely and the lubricating oil can be managed appropriately.

In the present invention, as means for determining the degradation/alteration state of a lubricating oil, dielectric constants or electrostatic capacitances of a lubricating oil at two or more different frequencies are measured.

It should be noted that the term "two or more" in the above-mentioned description includes the case of "two" and the case of "three or more", and there is no particular constraint on the upper limit of the number of measurements. More specifically, electrostatic capacitances $C_1, C_2, \ldots C_n$ at frequencies $H_1, H_2, \ldots H_n$ are measured, and dielectric constants $\epsilon_1, \epsilon_2, \ldots \epsilon_n$ are obtained based on the measured electrostatic capacitances.

If dielectric constants or electrostatic capacitances of a lubricating oil at two or more different frequencies are measured, a rate of a change in dielectric constant or electrostatic capacitance with respect to a change in frequency can be measured, and the degradation/alteration state of a lubricating oil can be predicted as described later. Further, if dielectric constants or electrostatic capacitances are measured at three or more different frequencies, a change in dielectric constant or electrostatic capacitance with respect to a frequency can be grasped more widely and precisely.

It is necessary that at least one frequency (generally, the lowest frequency) ($H_1$) of the two or more different frequencies $H_1, H_2 \ldots H_n$ be in a range of 1 to 100 Hz. If the frequency ($H_1$) is more than 100 Hz, the dielectric constant or the electrostatic capacitance may not change sufficiently depending upon the concentration of a polar substance generated due to the degradation/alteration of a lubricating oil, and hence, the degradation/alteration states of lubricating oils cannot be discriminated or determined precisely. Thus, the frequency ($H_1$) is preferably 80 Hz or less, more preferably 60 Hz or less.

In contrast, when the frequency ($H_1$) is less than 1 Hz, the value of a dielectric constant or an electrostatic capacitance to be measured is not stable, which makes it necessary to take a considerable time for measurement, and a measured value having reproducibility cannot be obtained due to a large amount of noise. Therefore, the frequency ($H_1$) is preferably 5 Hz or more, more preferably 10 Hz or more.

Further, based on the above-mentioned description, at least one frequency ($H_1$) of the two or more different frequencies is preferably in a range of 5 to 80 Hz, more preferably in a range of 10 to 60 Hz.

On the other hand, the frequency ($H_2$) other than the frequency ($H_1$) needs to be larger than the frequency ($H_1$) and in a range of 10,000 Hz or less. If the frequency is more than 10,000 Hz, the dielectric constant or the electrostatic capacitance may not change sufficiently depending upon the concentration of a polar substance generated due to the degradation/alteration of a lubricating oil, and hence, the degradation/alteration states of lubricating oils cannot be discriminated and determined precisely. Thus, the frequency ($H_2$) is preferably less than 10,000 Hz, more preferably 1,000 Hz or less, still more preferably 500 Hz or less, particularly preferably 200 Hz or less.

The range of frequencies ($H_3$) ... ($H_n$) in the case of measuring dielectric constants and the like at three or more different frequencies may be selected in a range of more than ($H_2$) and 10,000 Hz or less, preferably 1,000 Hz or less.

In the present invention, the degradation/alteration state of a lubricating oil is determined based on the values of dielectric constants or electrostatic capacitances at two or more different frequencies.

For example, the degradation/alteration state can be determined as follows by paying attention to two frequencies of the two or more frequencies. That is, a dielectric constant ($\in_1$) or an electrostatic capacitance ($C_1$) at the frequency ($H_1$) in a range of 1 to 100 Hz and a dielectric constant ($\in_2$) or an electrostatic capacitance ($C_2$) at the frequency ($H_2$) larger than the frequency ($H_1$) in a region of 10,000 Hz or less are obtained, and the degradation/alteration state of a lubricating oil is determined based on the value of ($\in_1$) or ($C_1$) or the value of ($\in_2$) or ($C_2$) and on the rate of a change in dielectric constant with respect to the frequency $[(\in_1-\in_2)/(H_2-H_1)]$ or the rate of a change in electrostatic capacitance with respect to the frequency $[(C_1-C_2)/(H_2-H_1)]$.

As described above, determining a degradation/alteration state is determining a degree of degradation/alteration and predicting a degradation/alteration mechanism (cause of degradation/alteration). It is generally preferred that the degree of degradation/alteration be determined based on the value of ($\in_1$) or ($C_1$). This is because, generally, a dielectric constant or an electrostatic capacitance at the smallest frequency of the measured frequencies shows the largest value, and thus, a change with time in dielectric constant or electrostatic capacitance can be recognized precisely. However, in some cases, the degree of degradation/alteration may be determined based on ($\in_2$) or ($Y_2$) or based on ($\in_2$) ... ($\in_n$) or ($C_3$) ... ($C_n$).

Regarding the degree of degradation/alteration, it is determined that the degradation/alteration of a lubricating oil has advanced as the value of the dielectric constant ($\in_1$) or the electrostatic capacitance ($C_1$) is larger. This is because the value of a dielectric constant or an electrostatic capacitance changes in accordance with the amount of a polar substance generated and mixed due to the degradation/alteration of a lubricating oil (mainly, a polar substance generated due to the oxidation/thermal degradation and a polar substance mixed in a lubricating oil).

As a method of predicting the lifetime of a lubricating oil based on the degradation/alteration degree (degree of degradation/alteration) of a lubricating oil obtained from the value of the dielectric constant ($\in_1$) or the electrostatic capacitance ($Y_1$) at the frequency ($H_1$), for example, it may be presumed that a lubricating oil has been degraded/altered at a time when the value of ($\in_1$) or ($Y_1$) has reached a set value previously determined in a preliminary experiment as in the measurement of an oil before and after a specification engine test, and a change with time of the dielectric constant ($\in_1$) or the electrostatic capacitance ($Y_1$) at the frequency ($H_1$) of a lubricating oil to be used is extrapolated and a period up to the set value may be presumed as a remaining lifetime.

Next, a method of predicting a degradation/alteration mechanism (cause of degradation/alteration) of a lubricating oil based on values of dielectric constants or electrostatic capacitances at two or more different frequencies is described.

As a method of predicting a degradation/alteration mechanism (cause of degradation/alteration) of a lubricating oil based on values of dielectric constants or electrostatic capacitances at two or more different frequencies, there is a method of predicting the degradation/alteration state of a lubricating oil based on a rate (magnitude) of a change in dielectric constant or electrostatic capacitance with respect to a frequency.

Specifically, for example, a rate of a change in dielectric constant with respect to a frequency $[(\in_1-\in_2)/(H_2-H_1)]$ or a rate of a change in electrostatic capacitance $[(C_1-C_2)/(H_2-H_1)]$ is considered.

In the case where $[(\in_1-\in_2)/(H_2-H_1)]$ or $[(C_1-C_2)/(H_2-H_1)]$ is considerably larger than the normal value (exceeds 200% compared with the normal value), it is presumed that, as a polar substance generated due to the degradation/alteration of a lubricating oil, in addition to a polar substance generated due to the oxidation/degradation, a polar substance generated due to other factors has been mixed (Degradation/alteration state I). It has been confirmed that such a degradation/alteration mechanism is found in a gasoline engine oil used in a gasoline engine.

In contrast, in the case where $[(\in_1-\in_2)/(H_2-H_1)]$ or $[(C_1-C_2)/(H_2-H_1)]$ is slightly larger than the normal value (within 200% of the normal value) but the increase in viscosity or deterioration in hue is recognized, it is presumed that, as a polar substance generated due to the degradation/alteration of a lubricating oil, another non-polar substance or weakly polar substance has been mixed as well as a polar substance generated due to the oxidation/degradation (Degradation/alteration state II). Degradation/alteration caused by such a degradation/alteration mechanism is recognized in the case where soot has been mixed in a diesel engine oil used in a diesel engine. In such a case, it is necessary to adjust the burning state in an engine and to take measures including the improvement of a soot trapping device.

The criterion for determining whether or not a rate of a change in dielectric constant or electrostatic capacitance with respect to a frequency is large may be set by performing a preliminary experiment of comparing calculated values of engine oils under different kinds of specifications before and after an engine test. In such a case, it is preferred that a viscometer or a hue meter be provided in a measuring device.

Thus, the degradation/alteration mechanism of a lubricating oil can be predicted. It should be noted that, in the present invention, in order to determine the above-mentioned degradation/alteration mechanism of a lubricating oil, the properties other than the dielectric constant or electrostatic capacitance may be measured to determine the degradation/alteration mechanism based on those properties.

Next, a measuring device preferred for measuring a dielectric constant or an electrostatic capacitance in the present invention is described.

Figure 3:
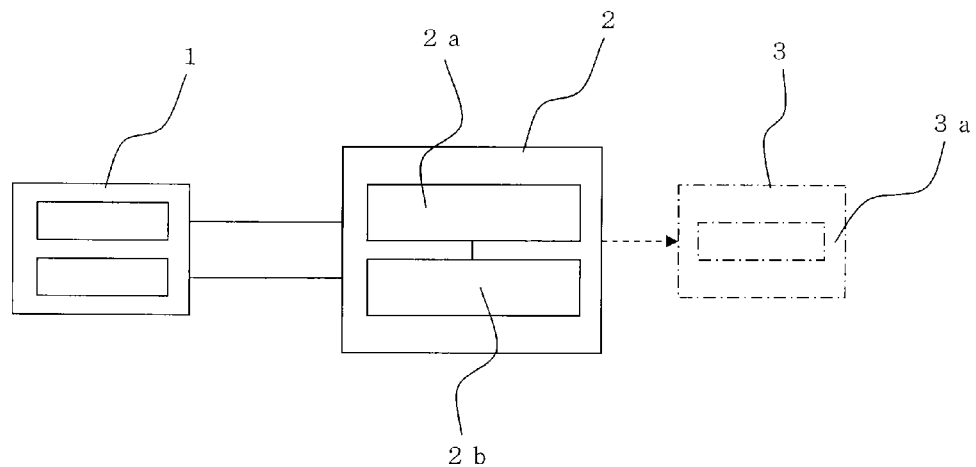

FIG. 3 is a conceptual diagram illustrating one example of the device for measuring a degree of degradation/alteration of a lubricating oil used in the method of measuring a degree of degradation/alteration of a lubricating oil of the present invention.

The device for measuring a degree of degradation/alteration of a lubricating oil includes a pair of electrodes 1 and an electrostatic capacitance measuring part 2 having an AC power source 2a for applying an AC voltage between the pair of electrodes, which is capable of controlling the frequency to a region of 100 Hz or less, and an electrostatic capacitance measuring circuit 2b for measuring an electrostatic capacitance between the electrodes. The measuring device may further include a dielectric constant calculating part 3 having a dielectric constant calculating circuit 3a for calculating a dielectric constant based on the electrostatic capacitance obtained in the electrostatic capacitance measuring part 2.

It is preferred that the AC power source 2a be capable of controlling the frequency to a region of 10 Hz or less, and it is more preferred that the AC power source 2a be capable of controlling the frequency to 1 Hz.

According to a method of measuring an electrostatic capacitance of a lubricating oil and a method of calculating a dielectric constant thereof, first, the pair of electrodes 1 are soaked in a lubricating oil, an AC voltage of an intended frequency $H_1$ is applied between the electrodes by the AC power source 2a of the electrostatic capacitance measuring part 2, and an electrostatic capacitance $C_1$ between the electrodes is measured by the electrostatic capacitance measuring circuit 2b. Then, if required, the electrostatic capacitance $C_1$ is converted into a dielectric constant $\in_1$ by the dielectric constant calculating circuit 3a. Similarly, an electrostatic capacitance $C_2$ at a different frequency $H_2$ is measured, and similarly, a dielectric constant $\in_2$ is calculated. It should be noted that the dielectric constant $\in$ and the electrostatic capacitance C have a relationship of the following Expression (I).

$$\in = C \times d/s \qquad (I)$$

(where d represents a distance between the pair of electrodes, and s represents a surface area of the electrode.)

Further, it is preferred that the measured voltage in the above-mentioned electrostatic capacitance measurement be set in a range of 0.1 to 10 $V_{p\text{-}p}$.

As the pair of electrodes 1 in FIG. 3, comb-shaped electrodes are preferred, and comb-shaped minute electrodes are particularly preferred. Further, as the electrostatic capacitance measuring part 2 and the dielectric constant calculating part 3, an LCR meter or a C meter can be used.

According to the method of measuring the electrostatic capacitance C of a lubricating oil directly and obtaining the dielectric constant $\in$ from the value of the electrostatic capacitance C as described above, the device is simple and an electrostatic capacitance and a dielectric constant of a lubricating oil can be measured and calculated easily at low cost with high precision.

Particularly, in the case where comb-shaped electrodes are used as the pair of electrodes 1, there is an effect that an evaluation device can be miniaturized, and the degree of degradation/alteration of a lubricating oil can be measured only by extracting a trace amount of a sample oil (lubricating oil). Simultaneously, because it is easy to observe the sample oil in measurement, there is also an effect that supplementary information on a degree of degradation/alteration of a lubricating oil and a degradation/alteration mechanism can be obtained from the external appearance (color) and odor of the sample oil.

FIG. 4 is a conceptual diagram illustrating another example of the device for measuring a degree of degradation/alteration of a lubricating oil used for carrying out the method of measuring a degree of degradation/alteration of the present invention.

This measuring device is a device for measuring a degree of degradation/alteration of a lubricating oil, including a pair of electrodes 11, an AC power source 12 capable of controlling a frequency to a region of 1 Hz, an ammeter 13, a voltmeter 14, and an electrostatic capacitance measuring part 15 having a complex impedance calculating circuit 15a and an electrostatic capacitance calculating circuit 15b. The measuring device may further include a dielectric constant calculating part 16 having a dielectric constant calculating circuit 16a.

According to a method of measuring and calculating an electrostatic capacitance or a dielectric constant, first, the pair of electrodes 11 are soaked in a lubricating oil, and an AC voltage of a frequency $H_1$ is applied between the electrodes by the AC power source 12 capable of controlling the frequency to a region of 1 Hz. Then, a complex impedance of a lubricating oil is calculated by the complex impedance calculating circuit 15a from a current I and a voltage V measured by the ammeter and the voltmeter and a phase difference between the current and the voltage. Then, the electrostatic capacitance calculating circuit 15b calculates a capacitance component (that is, an electrostatic capacitance) $C_1$ from a value of an imaginary part (reactance) $Z_C$ of a real part (resistance component) $Z_R$ and the imaginary part (reactance) $Z_C$ constituting the impedance (see the following Expression (II)). Then, if required, a dielectric constant $\in_1$ is obtained from a value of the electrostatic capacitance $C_1$ by the dielectric constant calculating circuit 16a. Further, similarly, an electrostatic capacitance $C_2$ at a frequency $H_2$ is measured.

$$\begin{aligned} Z &= V/I \\ &= Z_R + Z_C = R + 1/j\omega C \end{aligned} \qquad (II)$$

(where Z represents an impedance, $Z_R$ represents a resistance component, $Z_C$ represents an imaginary part of the impedance, R represents a resistance, j represents an imaginary unit, $\omega$ represents an AC angular frequency, and C represents an electrostatic capacitance.)

It is preferred that the measured voltage in the above-mentioned electrostatic capacitance measurement be set in a range of 0.1 to 10 $V_{p\text{-}p}$.

The above-mentioned device for measuring a degree of degradation/alteration of a lubricating oil used for carrying out the present invention can be incorporated in a part of an operation monitoring system of a machine and a device such as an engine so as to always monitor the degradation/alteration state of a lubricating oil. Thus, the device for measuring a degree of degradation/alteration of a lubricating oil of the present invention can be used as a lubricating oil monitoring system for a machine and a device.

EXAMPLES

Examples of the present invention are described further, but the present invention is not limited by these examples.

Example

Figure 1:
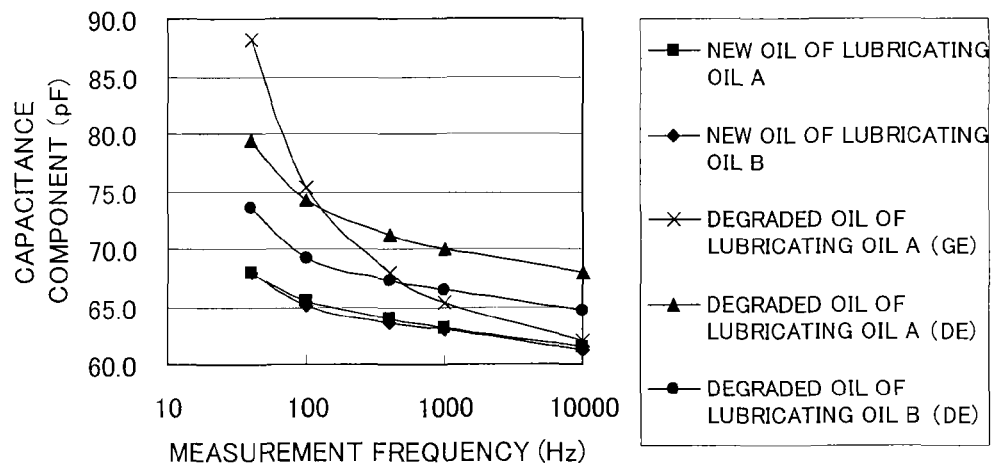
[FIG. 1] A diagram (graph) showing a relationship between a capacitance component (electrostatic capacitance) of a lubricating oil used in an example and a frequency.

With the use of the device for measuring a degree of degradation/alteration of a lubricating oil (electrostatic capacitance measuring part and dielectric constant calculating part) illustrated in FIG. 4, capacitance components [electrostatic capacitance (pF)] at frequencies of 40, 100, 150, 1,000, and 10,000 Hz were measured regarding the following sample oils (i) to (v) (new oil and degraded/altered oil) under the following measurement conditions. FIG. 1 shows the results as a change in capacitance component (electrostatic capacitance) with respect to a frequency.

(Measurement Conditions)

Electrodes: comb-shaped minute electrodes
Measured voltage: 1 $V_{p-p}$ (Measurement Samples)

(i) New oil of lubricating oil A (ashless engine oil)
(ii) New oil of lubricating oil B (CD-class diesel engine oil)
(iii) Degraded oil (GE) of lubricating oil A [used in gasoline engine (GE) to be degraded: mixed with a polar substance]
(iv) Degraded oil (DE) of lubricating oil A [used in diesel engine (DE) to be degraded: mixed with soot]
(v) Degraded oil (DE) of lubricating oil B [used in diesel engine (DE) to be degraded: mixed with soot]

Further, assuming that capacitance components (electrostatic capacitances) at the frequencies of 40 Hz and 100 Hz are ($C_{40}$) and ($C_{100}$), a rate of a change in capacitance component with respect to a frequency was calculated by the following expression.

Rate of change in capacitance component (electrostatic capacitance) with respect to frequency (%)=[($C_{40}-C_{100}$)/(100−40)]×100

Similarly, assuming that dielectric constants obtained from the capacitance components at the frequencies of 40 Hz and 100 Hz are $\in_{40}$ and $\in_{100}$, a rate of a change in dielectric constant with respect to a frequency can be calculated by the following expression.

Rate of change in dielectric constant with respect to frequency (%)=[($\in_{40}-\in_{100}$)/(100−40)]×100

Herein, Table 1 shows the results of the rate of a change in capacitance component with respect to a frequency.

rate of the latter is small. Further, the degraded/altered oil of the lubricating oil B of the sample oil (v) obtained by degrading/altering the new oil of the lubricating oil B as the sample oil (ii) in a diesel engine similarly to the sample oil (iv) also shows a rate of a change in capacitance component (electrostatic capacitance) with respect to a frequency similar to that the sample oil (iv).

Thus, the degradation/alteration mechanism (cause of degradation/alteration) of a lubricating oil can be predicted from a rate of a change in capacitance component (electrostatic capacitance) with respect to a frequency.

Further, it is understood that the degradation/alteration mechanism (cause of degradation/alteration) of a lubricating oil can also be predicted from a difference of rates of changes in capacitance components (electrostatic capacitances) at two or more frequencies other than 40 Hz and 100 Hz illustrated in FIG. 1.

Comparative Example

Figure 2:
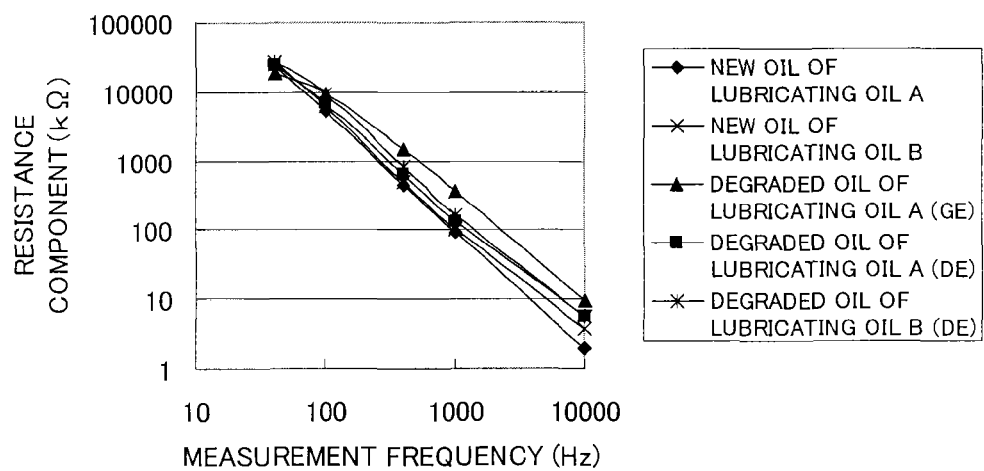
[FIG. 2] A diagram (graph) showing a relationship between a resistance component of a lubricating oil used in a comparative example and a frequency.

The sample oils used in the example were measured for a resistance component (Ω) of the impedance in place of a capacitance component (electrostatic capacitance) measured in the example. FIG. 2 shows the results as a change in resistance component with respect to a frequency. The measuring device, voltage, measurement frequencies, and sample oils that are used are the same as those of the example.

As shown in FIG. 2, no clear difference is recognized in a change in resistance component with respect to a frequency in the new lubricating oils as well as the degraded/altered lubricating oils of the sample oils (i) to (v). Thus, it is understood that a degradation/alteration mechanism of a lubricating oil cannot be predicted by this method.

The following is further understood from FIG. 1 of the example and FIG. 2 of the comparative example.

(1) The degree of degradation/alteration of a lubricating oil appears in a capacitance component (electrostatic capaci-

TABLE 1

|  |  | Sample oil (i) New oil of lubricating oil A | Sample oil (ii) New oil of lubricating oil B | Sample oil (iii) Degraded oil (GE) of lubricating oil A | Sample oil (iv) Degraded oil (DE) of lubricating oil A | Sample oil (v) Degraded oil (DE) of lubricating oil B |
|---|---|---|---|---|---|---|
| Capacitance component (pF) | $C_{40}$ | 68.0 | 67.5 | 88.2 | 79.5 | 73.6 |
|  | $C_{100}$ | 65.5 | 64.5 | 75.3 | 74.3 | 69.2 |
| Change rate of capacitance component (%) | [($C_{40} - C_{100}$)/(100 − 40)] × 100 | 4.2 | 5.0 | 21.5 | 8.7 | 7.3 |

The following is understood from FIG. 1 and Table 1.

Although the sample oil (i) and the sample oil (ii) are different in composition, the capacitance components (electrostatic capacitances) thereof have no difference among the frequencies of to 10,000 Hz and are smaller than those of any other degraded/altered oils.

Further, a rate of a change in capacitance component (electrostatic capacitance) with respect to a frequency varies between the sample oil (iii), in which a polar substance as a degraded/altered product has been mixed as a result of degradation/alteration of the lubricating oil A in a gasoline engine, and the sample oil (iv), in which soot in addition to the polar substance as a degraded/altered product have been mixed as a result of degradation/alteration of the lubricating oil A in a diesel engine. The rate of the former is large and the tance) of an impedance measured regarding the lubricating oil, but does not appear in a resistance component.

(2) The degree of degradation/alteration of a lubricating oil clearly appears in the capacitance component (electrostatic capacitance) in a lower frequency region, particularly in the capacitance component (electrostatic capacitance) in a range of 1 to 100 Hz.

(3) In the capacitance component (electrostatic capacitance) regarding a new oil of a lubricating oil, the difference caused by the difference in lubricating oils is hardly recognized.

(4) If the degradation/alteration condition varies, the behavior (change in electrostatic capacitance caused by a magnitude of the electrostatic capacitance and a change in frequency) of each capacitance component (electrostatic capacitance) varies even in the case of the same lubricating oil.

(5) The degradation/alteration state varies depending upon a lubricating oil even under the same degradation/alteration condition.

From the above-mentioned description, by measuring a capacitance component (electrostatic capacitance) at two or more different particular frequencies or dielectric constants calculated from the electrostatic capacitances, the degradation/alteration degree of a lubricating oil and the degradation/alteration mechanism can be predicted.

Industrial Applicability

According to the method of measuring a degree of degradation/alteration of a lubricating oil of the present invention, the degree of degradation/alteration of a lubricating oil can be measured easily and precisely, and at the same time, the degradation/alteration mechanism (cause of degradation/alteration) thereof can be predicted. Further, the device for measuring a degree of degradation/alteration of a lubricating oil of the present invention can determine the state of degradation/alteration of even a trace amount of sample oil, and further can be used effectively as a lubrication management system for a machine and a device such as an automobile engine.

The invention claimed is:

1. A method of measuring a degree of degradation/alteration of a lubricating oil, the method comprising:
    measuring a dielectric constant or electrostatic capacitance of a lubricating oil at two or more different frequencies; and
    determining a degradation/alteration state of the lubricating oil based on values of the dielectric constants or the electrostatic capacitances,
    measuring a dielectric constant ($\epsilon_1$) or an electrostatic capacitance ($C_1$) of the lubricating oil at $H_1$ and a dielectric constant ($\epsilon_2$) or an electrostatic capacitance ($C_2$) of the lubricating oil at $H_2$; and
    determining that the lubricating oil has been degraded/altered when a value of the dielectric constant ($\epsilon_1$) or the electrostatic capacitance ($C_1$) or the dielectric constant ($\epsilon_2$) or the electrostatic capacitance ($C_2$) has reached a set value; and predicting a degradation/alteration mechanism of the lubricating oil based on a rate of a change in dielectric constant with respect to the frequency $[(\epsilon_1-\epsilon_2)/(H_2-H_1)]$ or a rate of change in electrostatic capacitance with respect to the frequency $[(C_1-C_2)/(H_2-H_1)]$,
    wherein one frequency ($H_1$) of the two or more different frequencies is in a range of 5 to 80 Hz, and another frequency ($H_2$) is more than $H_1$ and in a range of 1,000 Hz or less.

2. The method of claim 1, wherein $H_1$ is in a range of 5 to 60 Hz.

3. The method of claim 1, wherein $H_1$ is in a range of 10 to 60 Hz.

4. The method of claim 3, wherein $H_2$ is more than $H_1$ and in a range of 500 Hz or less.

5. The method of claim 3, wherein $H_2$ is more than $H_1$ and in a range of 200 Hz or less.

6. The method of claim 1, wherein $H_2$ is more than $H_1$ and in a range of 500 Hz or less.

7. The method of claim 1, wherein $H_2$ is more than $H_1$ and in a range of 200 Hz or less.

8. A device, comprising:
    a pair of electrodes;
    an AC power source, which applies an AC voltage between the pair of electrodes under control of a frequency to a region of 100 Hz or less; and
    an electrostatic capacitance measuring part comprising an electrostatic capacitance measuring circuit, which measures an electrostatic capacitance between the pair of electrodes,
    wherein the electrostatic capacitance measuring circuit determines that the lubricating oil has been degraded/altered when a value of the dielectric constant ($\epsilon_1$) or the electrostatic capacitance ($C_1$) or a value of the dielectric constant ($\epsilon_2$) or the electrostatic capacitance ($C_2$) has reached a set value; and predicting a degradation/alteration mechanism of the lubricating oil based on a rate of change in dielectric constant with respect to the frequency $[(\epsilon_1-\epsilon_2)/(H_2-H_1)]$ or a rate of change in electrostatic capacitance with respect to the frequency $[(C_1-C_2)/(H_2-H_1)]$,
    wherein one frequency ($H_1$) of the two or more different frequencies is in a range of 5 to 80 Hz, and another frequency ($H_2$) is more than $H_1$ and in a range of 1,000 Hz or less.

9. The device of claim 8, further comprising:
    a dielectric constant calculating part comprising a dielectric constant calculating circuit, which calculates a dielectric constant based on the electrostatic capacitance obtained in the electrostatic capacitance measuring part.

10. The device of claim 8, wherein the pair of electrodes comprise comb-shaped electrodes.

11. A lubricating oil monitoring system, comprising:
    the device of claim 8.

12. The device of claim 8, being suitable for measuring a degree of degradation/alteration of a lubricating oil.

* * * * *